United States Patent [19]

Suzuki et al.

[11] Patent Number: 5,218,087
[45] Date of Patent: Jun. 8, 1993

[54] METHOD FOR MODIFYING MEDICAL MATERIALS OF LACTIC ACID POLYMERS

[75] Inventors: Masakazu Suzuki, Ayabe; Yoshikiyo Saito, Moriyama; Yoshikiyo Ikada; Shuon Hye H., both of Uji, all of Japan

[73] Assignee: Gunze Limited, Kyoto, Japan

[21] Appl. No.: 656,059

[22] PCT Filed: Jun. 20, 1990

[86] PCT No.: PCT/JP90/00814

§ 371 Date: Feb. 15, 1991

§ 102(e) Date: Feb. 15, 1991

[87] PCT Pub. No.: WO90/15629

PCT Pub. Date: Dec. 27, 1990

[30] Foreign Application Priority Data

Jun. 22, 1989 [JP] Japan .................................. 1-160484

[51] Int. Cl.$^5$ ............................. C08F 6/00; C08F 6/10
[52] U.S. Cl. .................................... 528/503; 528/354; 528/357; 528/501; 528/502
[58] Field of Search ................ 528/354, 361, 502, 503, 528/507; 623/16

[56] References Cited

U.S. PATENT DOCUMENTS 3,636,956 1/1972 Schneider .......................... 528/354
3,772,420 12/1968 Glick et al. ....................... 528/354

FOREIGN PATENT DOCUMENTS 449591 11/1971 Australia .
712555 9/1968 Belgium .
0199074 10/1986 European Pat. Off. .
0316992 5/1989 European Pat. Off. .
2635966 9/1990 France .
1048088 11/1966 United Kingdom .

Primary Examiner—John Kight, III
Assistant Examiner—Shelley A. Dodson
Attorney, Agent, or Firm—Armstrong, Westerman, Hattori, McLeland & Naughton

[57] ABSTRACT

Disclosed is a method for modifying a medical material of lactic acid polymer, the method comprising heat-treating the material at a temperature which is not lower than 100° C. and is lower than the melting point of the polymer for at least 10 minutes while continuously releasing the gas from the system.

5 Claims, No Drawings

METHOD FOR MODIFYING MEDICAL MATERIALS OF LACTIC ACID POLYMERS

FIELD OF THE INVENTION

The present invention relates to a method for modifying a medical material of lactic acid polymer.

BACKGROUND ART

Lactic acid polymers such as polylactic acid are absorbed into the living organism on in vivo hydrolysis, and because of this nature are used for various medical materials, for example, for surgical materials to be imbedded in the living body. These polymers are processed into monofilaments, threads, knits, nonwoven fabrics, woven fabrics, shaped bodies or the like to provide surgical sutures, artificial ligaments, artificial tendons, patches, meshes, bone-joining pins, plates, screws, stapler pins or the like. Since lactic acid polymers are gradually decomposed and absorbed in the living organism, they are known as suitable materials for artificial ligaments, bone-joining pins, artificial tendons, etc. which are generally employed for purposes in which healing takes a prolonged period of time.

This type of medical materials of lactic acid polymers are not satisfactory in the ability to retain the strength in the living organism because the medical material is diminished in the strength, particularly tensile strength, in a relatively short time after implantation in the living body, frequently posing medically unfavorable problems. In view of the possible problems, there is a need for medical materials of lactic acid polymers which can retain sufficient strength in the living body over a longer period of time when used for medical applications.

DISCLOSURE OF THE INVENTION

The present invention provides a modified medical material of lactic acid polymer which can retain sufficient strength in the living organism over a prolonged period of time and a process for preparing the same.

More specifically the present invention provides a method for modifying a medical material of lactic acid polymer, the method comprising heat-treating the material at a temperature which is not lower than 100° C. and is lower than the melting point of the polymer for at least 10 minutes while continuously releasing the gas from the system.

The present inventors' research revealed the following. When a medical material of lactic acid polymer is heat-treated at a temperature which is not lower than 100.C but is lower than the melting point of the polymer for at least 10 minutes while releasing the gas from the system, the medical material is thermally favorably modified and made to retain sufficient strength in the living body over a long period of time. The medical material of lactic acid polymer is pronouncedly improved in the ability to retain the strength in vivo, only when heat-treating the material at not lower than 100° C. for at least 10 minutes while continuously releasing the gas from the system. If the heat-treatment is done at a temperature of lower than 100° C., or for a period of shorter than 10 minutes, or in the system which is unable to continuously release the gas, although under otherwise favorable conditions, the obtained medical material is not fully improved in the ability to retain the strength in the living organism and is reduced in the strength in the living body in a relatively short period of time. While it has yet to be completely clarified why the heat treatment in the invention can pronouncedly improve the ability to retain the strength in the living organism, this is presumably because the undesired impurities such as the oligomer of a monomer, dimer or the like are removed from the polymer on vaporization by heating under the above-specified conditions, and also because the structure, particularly the crystalline structure, of the polymer undergoes some change by heating at 100° C. or higher for 10 minutes or more, thereby properly reducing the hydrolyzing rate of the polymer in the living organism.

Examples of lactic acid polymers to be modified according to the present invention are poly-L-lactic acid, poly-D-lactic acid, poly-D,L-lactic acid, a stereocomplex of poly-D-lactic acid and poly-L-lactic acid and like polylactic acids; a copolymer of lactic acid and a polymerizable monomer other than lactic acids which is capable of producing an in vivo absorbable polymer such as glycolic acid, paradioxanone, caprolactone and the like; and mixtures of polylactic acids and other in vivo absorbable polymers than polylactic acids, such as polyglycolic acid, polyparadioxanone, polycaprolactone and the like. Among them, polylactic acids are preferred. The lactic acid polymers for use in the invention include those having a wide range of molecular weight. The lactic acid polymer is imparted a reduced molecular weight by fusing in molding or spinning, but is substantially not given a reduced molecular weight by the heat treatment in the invention at a temperature below the melting point of the polymer. A preferred molecular weight of the material is in the range of about 60,000 to about 500,000, preferably about 70,000 to about 100,000, as determined in terms of the end product obtained by the heat treatment in the invention. Therefore it is desirable to select a lactic acid polymer as the starting material from which the end product having a molecular weight in the foregoing range can be produced. The molecular weight referred to herein is a value given by dissolving a lactic acid polymer in chloroform to a concentration of about 0.2 g/dl, diluting the solution with chloroform, and determining the intrinsic viscosity [$\eta$] of the dilute solution by the following equation to give a viscosity-average molecular weight:

$$[\eta] = KM\alpha$$

$$K = 5.45 \times 10^{-4}$$

$$\alpha = 0.73$$

According to the present invention, the heat treatment is effected on a product of lactic acid polymer in a proper form such as monofilaments, threads, knits, nonwoven fabrics, woven fabrics, shaped bodies or the like. The product of lactic acid polymer to be heat-treated may be either a finished medical article or a semi-fabricated product. For example, in forming a surgical suture, filaments may be heat-treated and subsequently processed into a thread, or alternatively a thread of filaments may be heat-treated. When required, the filaments or the thread may be stretched before the heat treatment. The stretching is conducted at room temperature or at an elevated temperature to achieve stretching to about 20 times or less, preferably about 2 to about 6 times. The stretching time is usually 30 seconds or less.

The heat treatment is essentially carried out in the invention at a temperature of 100° C. or higher for at least 10 minutes while releasing the gas from the system. When the heating temperature is lower than 100° C, the obtained medical material of lactic acid polymer may be imparted an improved initial strength but not an enhanced ability to retain the strength in the living organism. This is presumably because the heating at 100° C. or higher results in the evaporation of impurities in the polymer and also in certain desired thermal modification of the polymer in the crystalline structure. Therefore the heat treatment is essentially performed at a temperature of 100° C. or higher and lower than the melting point of the polymer. The heat treatment may be conducted at preferably 155° C. or lower, more preferably 105° to 155° C. to avoid the undesired thermal decomposition. Likewise when the heat-treating time is shorter than 10 minutes, the medical material of lactic acid polymer is not fully improved in the ability to retain the strength in the living organism. A preferred heat-treating time, which is suitably determinable depending on the heating temperature and the form of the medical material to be heat-treated, must be sufficient to vaporize the impurities in the polymer and to induce the thermal modification of the polymer in the crystalline structure, thereby reducing the hydrolyzing rate of the polymer in the living organism. A desirable heat-treating time is in the range of 15 to 240 minutes, which, however, may be extended depending on the form of the material to be heat-treated. It is also critical in the invention that the heat treatment be effected while continuously releasing the gas from the system. The continuous discharge of the gas can positively remove the vaporized impurities in the polymer from the system and can increase the synergistic effect of modifying the material. When the heat treatment is done in a system as in a closed one from which the impurities in the polymer can not be eliminated as desired, an enhanced initial strength can not be given and only a poor ability to retain the strength in the living organism is imparted. The heat treatment is preferably conducted in concurrence with exhaustion or suction of air to continuously discharge the gas from the system. The exhaustion or suction of air is performed by, for example, an exhaust-type hot-air dryer adapted to achieve a concurrent supply and discharge of air, a vacuum dryer adapted only to draw in air, or like means. A releasing condition suited for the exhaust-type hot-air dryer is such that the air is discharged in a quantity of at least 0.5 l/min·l, preferably at least 3 l/min·l. The suction condition, namely reduced pressure condition, for the vacuum dryer is 10 mmHg or less, preferably 1 mmHg or less.

The present invention will be described below in greater detail with reference to the following examples.

EXAMPLES

Example 1

Poly-L-lactic acid pellets having a molecular weight of 388,000 were forced through 12 spinnerets at a spinning temperature of 240° C. to form a yarn of 12 filaments. The obtained yarn was stretched to 5 times at 130° C., and the resulting yarn was braided by a braiding apparatus having eight feeders, producing a 430-denier braid. The braid was wound on a bobbin of stainless steel having a diameter of 3 cm and was heat-treated at the temperatures and for the periods indicated below in Table 1 while releasing the gas in an amount of 4.5 l/min·l by an air supply/discharge type hot-air dryer (adapted to achieve automatic, concurrent air supply and discharge).

Table 1 also shows the initial strength of the thus obtained braid and the ability thereof to retain the strength. The braid had a molecular weight of 68,000. The strength of the braid and the ability thereof to retain the strength were measured by the following methods.

Strength

The tensile strength was measured at a crosshead speed of 10 cm/min (5-cm distance between the holding means of the chuck).

Ability to Retain Strength

A sample was immersed in a physiological saline containing PBS (a phosphate buffer saline comprising 0.1 mole of a phosphate buffer adjusted to a pH of 7.4 and 0.8 wt. % of NaCl) at 37° C. or 50° C. in a bath ratio of 1:500. The sample was withdrawn after a lapse of the specified period, and the strength thereof was measured.

TABLE 1

| Heat-treating conditions Air supply/discharge type hot-air dryer | | In vitro at 37° C. | | | | | | |
|---|---|---|---|---|---|---|---|---|
| | | | Time elapsed (week) | | | | | |
| Temp (°C.) | Time (min) | Initial | 1 | 2 | 3 | 4 | 5 | 10 |
| Not treated | | 1143(g) | 1047 (91.6)(%) | 858 (75.1) | 718 (52.8) | 610 (53.4) | 578 (50.6) | — |
| 70 | 15 | 1317 | 1055 (80.1) | 844 (64.1) | 727 (55.2) | 603 (45.8) | 568 (43.1) | — |
| | 30 | 1410 | 1096 (77.7) | 810 (57.4) | 693 (49.1) | 641 (45.1) | 626 (44.4) | — |
| | 60 | 1447 | 1088 (75.2) | 968 (66.9) | 792 (54.7) | 672 (46.4) | 613 (42.4) | — |
| | 120 | 1351 | 1080 (79.9) | 924 (68.4) | 727 (53.8) | 630 (46.4) | 606 (44.9) | — |
| 105 | 5 | 1390 | 1213 (87.3) | 1123 (80.8) | 1066 (76.7) | 937 (67.4) | | |
| | 10 | 1383 | 1319 (95.4) | 1328 (96.0) | 1325 (95.8) | 1259 (91.0) | | 1243 (89.9) |
| | 15 | 1375 | 1320 (96.0) | 1323 (96.2) | 1327 (96.5) | 1246 (90.6) | | 1284 (93.4) |
| | 30 | 1382 | 1336 (96.7) | 1359 (98.3) | 1281 (92.7) | 1210 (87.6) | — | 1183 (85.6) |
| 105 | 60 | 1405 | 1286 | 1363 | 1225 | 1298 | — | 1285 |

TABLE 1-continued

| Heat-treating conditions Air supply/discharge type hot-air dryer | | | In vitro at 37° C. | | | | | |
|---|---|---|---|---|---|---|---|---|
| | | | Time elapsed (week) | | | | | |
| Temp (°C.) | Time (min) | Initial | 1 | 2 | 3 | 4 | 5 | 10 |
| | 120 | 1389 | (91.5) 1336 (96.2) | (97.0) 1303 (93.8) | (87.2) 1295 (93.2) | (92.4) 1255 (90.4) | | (84.2) 1283 (92.4) |
| 135 | 15 | 1283 | 1310 (102.1) | 1317 (102.7) | | | | 1281 (99.8) |
| | 30 | 1321 | 1320 (99.9) | 1338 (101.3) | — | — | — | 1322 (100.1) |
| | 60 | 1334 | 1328 (99.6) | 1344 (100.7) | — | — | — | 1313 (98.4) |
| | 120 | 1349 | 1260 (93.4) | 1310 (97.1) | — | — | — | 1245 (92.3) |

Values in the upper row: strength (g)
Values in the lower row: percent retention of strength (%)

Table 1 reveals the following. When heat treatment is conducted at a temperature of lower than 100° C., the initial strength is improved, but the ability to retain the strength in a physiological saline is deteriorated, that is, only less than 50% of the strength is retained in 5 weeks. On the other hand, when heat treatment is carried out in accordance with the present invention at a temperature of not lower than 100° C. for not less than 10 minutes while discharging the gas, the initial strength is improved nd 80% or more of strength is retained in the living organism even in 10 weeks.

Example 2

Poly-L-lactic acid pellets having a molecular weight of 440,000 were forced through 12 spinnerets at a spinning temperature of 240° C. to form a yarn of 12 filaments. The obtained yarn was stretched to 4.0 times at 130° C. The resulting yarn was wound on an aluminum bobbin having a diameter of 4.5 cm and was heat-treated at 105° C. for 60 minutes while releasing the gas in an amount of 4.5 l/min·l by the same air supply/discharge type hot-air dryer as used in Example 1. The treated yarns were braided by a braiding apparatus with 8 feeders adapted to receive one yarn of 12 filaments in each feeder, forming a 370-denier braid. The ultimately obtained braid had a molecular weight of 73,000.

Table 2 below shows the strength of the braid and the ability thereof to retain the strength (long term) as determined in the same manner as in Example 1.

TABLE 2

| | In Vitro at 37° C. | | | | |
|---|---|---|---|---|---|
| Time elapsed (month) | 0 (Initial) | 3 | 7 | 11 | 15 |
| Strength g (%) | 1560 | 1457 (93.4) | 1481 (94.9) | 1355 (92.6) | 889 (57.0) |

Table 2 reveals that the braid heat-treated in accordance with the present invention retained 90% or more of the strength in 11 months, and 50% or more thereof even in 15 months.

Example 3

Poly-L-lactic acid pellets having a molecular weight of 485,000 were forced through 12 spinnerets at a spinning temperature of 240° C. to form a yarn of 12 filaments. The yarn was stretched to 4.3 times at 130° C. and wound on an aluminum bobbin having a diameter of 4.5 cm. The yarn was heat-treated under the conditions shown below in Table 3 using an air supply/discharge type hot-air dryer, a vacuum dryer and a closed-type dryer. The heat treatment using the air supply/discharge type hot-air dryer was conducted while releasing the gas in an amount of 4.5 l/min·l, and the treatment using the vacuum dryer was carried out under a reduced pressure of 1 mmHg. The treated yarns were braided by a braiding apparatus with 4 feeders adapted to receive one yarn of 12 filaments in each feeder, giving a 140-denier braid. Table 3 below shows the initial strength of the obtained braid (molecular weight 75,000) and the ability thereof to retain the strength as determined in the same manner as in Example 1.

TABLE 3

| | | | In vitro at 50° C. | | | | |
|---|---|---|---|---|---|---|---|
| Heat-treating conditions | | | | Time elapsed (week) | | | |
| Method | Temp (°C.) | Time (min) | Initial | 1 | 2 | 3 | 4 |
| Not treated | — | — | 525 (g) | 432 (82.3)(%) | 343 (65.3) | 300 (57.1) | 219 (41.7) |
| Air supply/discharge type dryer | 115 | 120 | 513 | 529 (103.1) | 496 (96.7) | 511 (99.6) | 503 (98.1) |
| Closed-type dryer | 115 | 120 | 467 | 357 (76.4) | 239 (51.2) | 224 (48.0) | 198 (42.4) |
| Vacuum dryer | 115 | 120 | 442 | 493 (111.5) | 456 (103.2) | 445 (100.7) | 449 (101.6) |
| | 115 | 1020 | 440 | 463 (105.2) | 461 (104.8) | 470 (106.7) | 463 (100.0) |

Table 3 shows that the heat treatment using the closed-type dryer even if conducted at 100° C. or higher for 10 minutes or longer resulted in the production of a braid having a poor ability to retain the strength, whereas the heat treatment done concurrently with gas release by exhaustion or aspiration significantly improved the ability of the braid to retain the strength.

Example 4

The braid prepared in Example 1 was wound on a stainless steel bobbin having a diameter of 3 cm and was heat-treated at 105° C. for 240 minutes while releasing the gas in an amount of 4.5 l/min·l by an air supply/discharge type hot-air dryer. Heat treatment was also carried out in the same manner at 90°·C. using a vacuum dryer under a reduced pressure of 1 mmHg. The initial strength of the braid and the ability thereof to retain the strength (in vivo at 37° C.) are shown below in Table 4.

The results show that even if the impurities were removed in the same ratio, a diminished ability to retain the strength was given by the heat treatment at lower than 100° C.

TABLE 4

| Heat-treating conditions | | Weight decreased (g) | Reduction rate (%) | Time elapsed (week) | | | | |
|---|---|---|---|---|---|---|---|---|
| | | | | Initial | 1 | 2 | 4 | 5 | 10 |
| Air supply/ discharge type hot-air dryer | 105° C. | 297.1/ 297.78 | 0.228 | 1330 | 1204 (90.5) | 1235 (92.9) | 1151 (86.5) | | 1095 (82.3) |
| Vacuum dryer | 90° C. | 298.83/ 299.5 | 0.224 | 1296 | 1261 (97.3) | 1152 (88.9) | 970 (78.4) | 855 (66.0) | 518 (40.0) |

Example 5

Poly-L-lactic acid pellets having a molecular weight of 298,000 were forced through one spinneret at a spinning temperature of 240° C. to form a 10,700-denier unstretched monofilament.

The monofilament was heat-treated under the heat-treating conditions shown below in Table 5 at 155° C. at a pressure of 1 mmHg for 1440 minutes using a vacuum dryer.

The thus obtained thread (molecular weight 71,000) had the initial strength and the ability to retain the strength as listed below in Table 5.

TABLE 5

| Heat-treating conditions | | In vitro at 50° C. | | | | | | | |
|---|---|---|---|---|---|---|---|---|---|
| Temp. (°C.) | Time (min.) | Initial | 1 | 3 | Days elapsed 7 | 10 | 14 | 21 | 28 |
| Not treated | | 5860 | 5370 (92) | 2820 (48) | | | | | |
| 155 | 1440 | 6090 | | | 5850 (96) | 5640 (93) | 5250 (86) | 5450 (89) | 5060 (83) |

Values in the upper row: strength (g)
Values in the lower row: percent retention of strength (%)

We claim:

1. A method for improving the tensile strength retention properties of a medical material made of a lactic acid polymer, which comprises heating the material for at least 10 minutes at a temperature between 100° C. and the melting point of the polymer in a continuous current of hot air at a flow rate of at least 0.5 l/min·l.

2. A method according to claim 1, wherein the lactic acid polymer is a polylactic acid.

3. A method according to claim 1, wherein the temperature of heating is 105° to 155° C.

4. A method according to claim 1, wherein the material is heated for 15 to 240 minutes.

5. The medical material made of a lactic acid polymer prepared by the method of claim 1.

* * * * *

UNITED STATES PATENT AND TRADEMARK OFFICE
CERTIFICATE OF CORRECTION

PATENT NO. : 5,218,087
DATED : June 8, 1993
INVENTOR(S) : SUZUKI et al.

It is certified that error appears in the above-identified patent and that said Letters Patent is hereby corrected as shown below:

On the cover page, Item [75], third and fourth inventors' names are misspelled: "Yoshikiyo" should be --Yoshito--; and, "Shuon Hye H." should be --Shuon Hyu Hyon--.

Signed and Sealed this

Twenty-fourth Day of May, 1994

Attest:

BRUCE LEHMAN

*Attesting Officer*      *Commissioner of Patents and Trademarks*